United States Patent
Schuessler et al.

(10) Patent No.: US 9,382,508 B2
(45) Date of Patent: Jul. 5, 2016

(54) METHOD AND BIOREACTOR FOR THE CULTIVATION OF MICROORGANISMS

(75) Inventors: Stephan Schuessler, Caldern (DE); Eugene J. A. Roebroeck, GG Voorhout (NL); Sander H. E. Hazewinkel, HD Rotterdam (NL); Obbo J. H. Hazewinkel, BG Zoetermeer (NL)

(73) Assignees: LGem B.V., Vorhout (NL); Georg Fischer Piping Systems Ltd., Schaffhausen (CH)

( * ) Notice: Subject to any disclaimer, the term of this patent is extended or adjusted under 35 U.S.C. 154(b) by 0 days.

(21) Appl. No.: 13/984,629

(22) PCT Filed: Feb. 10, 2012

(86) PCT No.: PCT/EP2012/052272
§ 371 (c)(1),
(2), (4) Date: Oct. 3, 2013

(87) PCT Pub. No.: WO2012/107544
PCT Pub. Date: Aug. 16, 2012

(65) Prior Publication Data
US 2014/0017769 A1    Jan. 16, 2014

(30) Foreign Application Priority Data
Feb. 11, 2011    (EP) .................... 11001124

(51) Int. Cl.
| | | |
|---|---|---|
| *C12N 1/12* | (2006.01) |
| *C12M 1/04* | (2006.01) |
| *C12M 1/00* | (2006.01) |
| *A01G 33/00* | (2006.01) |
| *C12M 1/12* | (2006.01) |

(52) U.S. Cl.
CPC ............... *C12M 21/02* (2013.01); *A01G 33/00* (2013.01); *C12M 23/06* (2013.01); *C12M 23/22* (2013.01); *C12M 29/06* (2013.01); *C12M 29/18* (2013.01); *C12N 1/12* (2013.01)

(58) Field of Classification Search
None
See application file for complete search history.

(56) References Cited

U.S. PATENT DOCUMENTS

| | | | |
|---|---|---|---|
| 2006/0025545 A1* | 2/2006 | Brant et al. ..................... 526/64 |
| 2010/0068779 A1* | 3/2010 | Wells et al. .................... 435/167 |
| 2010/0144023 A1* | 6/2010 | Weaver et al. ............. 435/292.1 |
| 2011/0159575 A1 | 6/2011 | Fernandez et al. |
| 2011/0281339 A1* | 11/2011 | Riley ..................... C12M 21/02 435/257.1 |
| 2012/0021498 A1 | 1/2012 | Muller-Feuga |

FOREIGN PATENT DOCUMENTS

| | | |
|---|---|---|
| DE | 102005062726 A1 | 7/2007 |
| EP | 2258463 A1 | 12/2010 |
| WO | 2009051480 A2 | 4/2009 |
| WO | 2010109108 A1 | 9/2010 |

OTHER PUBLICATIONS

Tredici, M.R., and Zittelli, G.C. "Efficiency of Sunlight Utilization: Tubular Versus Flat Photobioreactors", Biotechnology and Bioengineering 1998, vol. 57, pp. 187-197.*

* cited by examiner

*Primary Examiner* — Renee Claytor
*Assistant Examiner* — Michelle F Paguio Frising
(74) *Attorney, Agent, or Firm* — Bachman & LaPointe, P.C.

(57) ABSTRACT

A method for the cultivation of microorganisms, especially phototrophic microorganisms in a bioreactor or photobioreactor, wherein bicarbonate ions and carbonate ions or a cation surplus concentration in the culture medium is added. A tubular bioreactor and photobioreactor is disclosed for carrying out the method.

16 Claims, 2 Drawing Sheets

METHOD AND BIOREACTOR FOR THE CULTIVATION OF MICROORGANISMS

BACKGROUND OF THE INVENTION

The invention relates to a method for the cultivation of organisms, especially phototrophic microorganisms in a bioreactor or photobioreactor, wherein bicarbonate ions and carbonate ions or a cation surplus concentration in the culture medium is added. The invention also relates to a tubular bioreactor and photobioreactor wherein the method can be achieved and the use of bioreactors, photobioreactors, tubes and pipes in a method according to the present invention.

Cultivation of phototrophic microorganisms like algae and cyanobacteria in open ponds and raceways is well developed but only a few species can be maintained in traditional open systems. Fully closed photobioreactors (PBR) provide opportunities for monoseptic culture of the microorganisms with specifically adapted culturing conditions. There are different types of photobioreactors like flat plate-PBRs, annular PBRs, e.g. bubble column PBRs and tubular PBRs. These can be further categorized according to orientation of tubes or panels, the mechanism of circulating the culture, the method used to provide light, the type of gas exchange system, the arrangement of the individual growth units, and the materials of construction employed. In the photobioreactor the microorganisms are suspended in a liquid medium. Photobioreactors allow the microorganisms to be illuminated either by natural sunlight or by artificial light sources. A typical photobioreactor is a three-phase system, consisting of a liquid phase, which is the culture medium, the cells as the solid phase and a gas phase. Light, which is the unique feature of photobioreactors is a superimposed radiation field, is sometimes called "the fourth phase" (C. Posten; Eng. Life Sci. 2009, 9, No. 3, pages 165-177).

Of the many designs of closed photobioreactors, devices with tubular solar collectors are the most promising and most widely used commercial systems (E. Molina et al.; Journal of Biotechnology 92 (2001); pages 113-131 and D. Briassoulis et al.: Bioresour. Technol. 101 (2010); pages 6768-6777).

Cultivation of phototrophic microorganisms in photobioreactors for industrial applications is highly dependent on the control of cultivation conditions. The design of the photobioreactors refers mainly to a good availability of light for the microorganisms. Also the pH is one of the major parameters effecting the performance of the microbial population. Production or consumption of $CO_2$ by microorganisms have strong effects on the pH of the cultivation medium.

When illuminated, photosynthesis occurs in the phototrophic microorganisms, enabling the production of carbohydrates from $CO_2$ and $H_2O$. The carbohydrates thus formed enables growth of the organism. This is called autotrophic growth. Due to the photosynthesis process $CO_2$ is consumed by the suspended microorganism, while $O_2$ is produced. The withdrawal of $CO_2$ by the phototrophic microorganisms from the liquid phase causes an increase of the pH of the liquid phase, while the production of oxygen causes an increase of the level of dissolved oxygen in the liquid phase.

In the dark photosynthesis will not occur. Due to respiration $O_2$ will be consumed by the suspended microorganism, while $CO_2$ is produced. The withdrawal of $O_2$ by the microorganisms from the liquid phase will cause a decrease of the level of dissolved $O_2$ in the liquid phase, while the production of $CO_2$ will cause a decrease of the pH.

In order to control pH and dissolved oxygen level of the liquid phase transfer of $O_2$ and $CO_2$ from the liquid phase to the gas phase and vice versa is required. Therefore microorganism cultures in photobioreactors are aerated. In the case of upright liquid containers this is done by injecting gas at the bottom of the reactor. In tubular photobioreactors aeration and degassing is achieved either in the airlift part or, in cases a pump is used for circulating the liquid medium, in a tank which is part of the liquid circuit. This tank is referred to as buffer tank, collection tank, circulation tank or degassing tank. $CO_2$ is fed to upright liquid containers by sparging $CO_2$ or $CO_2$ enriched air directly into the liquid medium at the bottom of the reactor or in the aeration gas flow. In tubular reactors $CO_2$ is commonly injected into the liquid circuit, directly after the air lift part or just before the circulation pump. DE 10 2005 062 726 A1 describes a photobioreactor having devices for circulating the gas in the systems. WO 2010/109108 A1 describes a photobioreactor setting up a two-phase gas/liquid flow in horizontal tubes.

Formation of a gradient of dissolved oxygen and pH between the gas inlet and the gas outlet along the main flow axis of the medium is a problem, especially in tubular reactors. These problems increase with increasing biomass concentrations and increasing light intensities, leading to high volumetric productivities. But high volumetric productivities in term of grams of biomass formed per liter per day are required to improve on the economy of the process.

Of equal importance is enhancing mass transfer along the main axis of the photobioreactor, which is the axial direction in tubes or the upward direction in panel reactors or columns. However, input of mechanical energy by bubbling or pumping is limited to avoid shear stress and cell damage and because energy supply is a major issue in production costs.

The invention is based on the object of providing methods and photobioreactors avoiding the disadvantages of methods and photobioreactors known in the state of the art.

The invention is based also on the object of providing methods and photobioreactors to cultivate phototrophic microorganisms resulting in higher yields of biomass and/or in lower costs.

SUMMARY OF THE INVENTION

In accordance with the invention this object is in particularly achieved by the methods, tubular photobioreactors and uses disclosed hereinbelow.

In accordance with the invention this object is in particularly achieved by a method for the cultivation of organisms in a bioreactor, including the steps: a) providing a liquid culture medium containing the organisms in the bioreactor and b) cultivating the organisms in the bioreactor, wherein the liquid culture medium contains a bicarbonate buffer system containing bicarbonate ions and/or carbonate ions in an amount of at least 2 mM, more preferably more than 2 mM, even more preferably to at least 3 mM (referred to the sum of bicarbonate ions and carbonate ions) and wherein during at least a time segment of step b) the liquid culture medium is moved, characterized in that during at least a time segment of step b) a gas phase containing at least 0.2 vol.-% $CO_2$ is introduced into the culture medium.

In accordance with the invention this object is in particularly achieved also by a method for the cultivation of organisms in a bioreactor, including the steps: a) providing in the bioreactor a liquid culture medium containing the organisms and b) cultivating the organisms in the bioreactor, wherein the liquid culture medium contains a bicarbonate buffer system and wherein during at least a time segment of step b) the liquid culture medium is moved and wherein during at least a time segment of step b) a gas phase containing at least 0.2 vol.-% $CO_2$ is introduced into the culture medium, characterized in that before and/or during step b) cations are added to the liquid culture medium in a concentration of at least 1 mM.

According to a preferred embodiment of the invention the organisms are microorganisms.

According to a preferred embodiment of the invention the organisms are autotrophic organisms. According to a preferred embodiment of the invention the organisms are autotrophic microorganisms. According to a preferred embodiment of the invention the organisms are heterotrophic organisms. According to a preferred embodiment of the invention the organisms are heterotrophic microorganisms.

According to an alternative embodiment of the invention the organisms are a mixture of autotrophic and heterotrophic organisms, especially autotrophic and heterotrophic microorganisms.

According to a preferred embodiment of the invention the bioreactor is a photobioreactor and the organisms are phototrophic organisms.

According to a preferred embodiment of the invention the phototrophic organisms are microorganisms. According to a preferred embodiment of the invention the phototrophic organisms are algae or cyanobacteria, particularly algae, especially microalgae. According to a preferred embodiment of the invention the phototrophic organisms are algae from the genus *Nannochloropsis*.

According to a preferred embodiment of the invention the phototrophic organisms, especially algae or cyanobacteria are cultivated to produce biomass, to fix $CO_2$ and/or to produce specific substances, for example Eicosapentaenoic acid or Docosahexaenoic acid.

The bioreactor used in the method according to the present invention can be any bioreactor, for example a tubular bioreactor.

The photobioreactor used in the method according to the present invention can be any photobioreactor, for example a flat plate photobioreactor, a bubble column photobioreactor or a tubular photobioreactor. According to a preferred embodiment of the invention the photobioreactor used in the method according to the present invention is a tubular photobioreactor. The tubular photobioreactor can have any geometry of the tubes. The tubular photobioreactor can have for example horizontal tubes or vertical tubes or variations of these types. The tubular photobioreactor can also be a helical-tubular photobioreactor.

According to a preferred embodiment of the invention the tubular bioreactor, especially photobioreactor used in the method according to the invention is a bioreactor, especially photobioreactor disclosed below, preferably a tubular bioreactor, especially photobioreactor according to the present invention.

The liquid culture medium can be moved by methods known in the state of the art, for example by a screw, by a pump or by an air-lift system.

According to a preferred embodiment of the invention the culture medium is moved by a pump or by an air-lift system through at least one tube of a tubular bioreactor or photobioreactor.

According to a preferred embodiment of the invention the culture medium is moved throughout step b).

Any suitable liquid culture medium for cultivating microorganisms, especially algae or cyanobacteria can be used. A person skilled in the art knows the requirements of culture media for specific microorganisms. The culture medium can contain already before the addition of cations in a concentration of at least 1 mM cations in an amount adapted to the requirements of the microorganism to be cultivated. For example a culture medium for saltwater algae contains more cations than a culture medium for freshwater algae.

According to a preferred embodiment of the invention the culture medium has a pH from at least pH 6 to at most pH 10, preferably from at least pH 7 to at most pH 9. According to a preferred embodiment of the invention the culture medium has a pH of around pH 8.4. Preferably the culture medium has such a pH during step b).

The culture medium contains a bicarbonate buffer system known in the state of the art. The bicarbonate buffer system is regulated by bicarbonate and carbonate present in the culture medium and the $CO_2$ present in the gas phase.

The gas phase can be any suitable gas phase, for example air, as long as it contains at least 0.2 vol.-% $CO_2$. According to a preferred embodiment of the invention the gas phase contains at least 0.5 vol.-% $CO_2$. According to a preferred embodiment of the invention the gas phase contains at least 1 vol.-% $CO_2$. According to a preferred embodiment of the invention the gas phase contains at least 0.2 vol.-% $CO_2$ and at most 50 vol.-% $CO_2$, more preferably at least 0.5 vol.-% $CO_2$ and at most 10 vol.-% $CO_2$. According to a preferred embodiment of the invention the gas phase contains at least 1 vol.-% $CO_2$ and at most 5 vol.-% $CO_2$. According to a preferred embodiment of the invention the gas phase contains around 2 vol.-% $CO_2$.

According to a preferred embodiment of the invention the gas phase is introduced into the culture medium throughout step b).

According to an alternative of the invention the culture medium contains carbonate ($CO_3^{2-}$) and bicarbonate ($HCO^{3-}$) in an amount of at least 3 mM. The amount refers to the sum of carbonate and bicarbonate contained in the culture medium.

According to a preferred embodiment of the invention carbonate and bicarbonate are present in the liquid culture medium in a concentration of at least 10 mM. According to a preferred embodiment of the invention carbonate and bicarbonate are present in the liquid culture medium in a concentration of at most 1000 mM. According to a preferred embodiment of the invention carbonate and bicarbonate are present in the liquid culture medium in a concentration of at most 100 mM. According to a preferred embodiment of the invention carbonate and bicarbonate are present in the liquid culture medium in a concentration of at least 1 mM to at most 1000 mM, more preferably of at least 10 mM to at most 100 mM. According to a preferred embodiment of the invention carbonate and bicarbonate are present in the liquid culture medium in a concentration of around 40 mM. The concentration refers to the sum of carbonate and bicarbonate contained in the culture medium.

According to a preferred embodiment of the invention the carbonate and bicarbonate are added before step b). Carbonate and bicarbonate can be even added before the microorganisms are inoculated in the culture medium. According to a preferred embodiment of the invention the carbonate and bicarbonate are added during step b).

According to a preferred embodiment of the invention the carbonate and bicarbonate are added in form of bicarbonate salts and/or carbonate salts. According to a preferred embodiment of the invention the carbonate and bicarbonate are added together with $Na^+$, $K^+$, $Mg^{2+}$ and/or $Ca^{2+}$.

According to a preferred embodiment of the invention the carbonate and bicarbonate are added by the addition of $NaOH$, $Na_2CO_3$ and/or $NaHCO_3$. According to a preferred embodiment of the invention the cations are added by the addition of $NaHCO_3$.

According to a preferred embodiment of the invention at least 10 mM to at most 100 mM $Na_2CO_3$ and/or $NaHCO_3$, more preferably only $NaHCO_3$ is added to have a carbonate and bicarbonate surplus concentration.

The addition of the carbonate and/or bicarbonate results in a cation surplus concentration.

According to an alternative of the invention cations are added to have a cation surplus concentration in the liquid culture medium.

According to a preferred embodiment of the invention cations are added to the liquid culture medium in a concentration of at least 10 mM. According to a preferred embodiment of the invention cations are added to the liquid culture medium in a concentration of at most 1000 mM. According to a preferred embodiment of the invention cations are added to the liquid culture medium in a concentration of at most 100 mM. According to a preferred embodiment of the invention cations are added to the liquid culture medium in a concentration of at least 1 mM to at most 1000 mM, more preferably of at least 10 mM to at most 100 mM. According to a preferred embodiment of the invention cations are added to the liquid culture medium in a concentration of around 40 mM.

According to a preferred embodiment of the invention the cations are added before step b). The cations can be even added before the microorganisms are inoculated in the culture medium. According to a preferred embodiment of the invention the cations are added during step b).

According to a preferred embodiment of the invention the cations are added as $Na^+$, $K^+$, $Mg^{2+}$ and/or $Ca^{2+}$. According to a preferred embodiment of the invention the cations are added in form of bicarbonate salts and/or carbonate salts. The cations can also be added in form of bases like NaOH or KOH.

According to a preferred embodiment of the invention the cations are added by the addition of NaOH, $Na_2CO_3$ and/or $NaHCO_3$. According to a preferred embodiment of the invention the cations are added by the addition of $NaHCO_3$.

According to a preferred embodiment of the invention at least 10 mM to at most 100 mM $Na_2CO_3$ and/or $NaHCO_3$, more preferably only $NaHCO_3$ is added to have a cation surplus concentration.

It was surprisingly found that the control of pH and mass transfer can be dramatically improved by increasing both the cation surplus concentration or the carbonate and bicarbonate concentration in the liquid phase and the $CO_2$ concentration in the gas phase, when cultivating phototrophic microorganisms in a photobioreactor.

For example, when $Na^+$ is chosen, the cation surplus concentration of the liquid phase can be increased by the addition of NaOH, $Na_2CO_3$ or $NaHCO_3$ to the medium. When aerated with a gas with a set/chosen $CO_2$ concentration of at least 0.2 vol.-% the pH of the liquid culture medium at equilibrium will be determined by the $Na^+$ concentration in the liquid phase and the $CO_2$ concentration in the gas phase. So, by increasing both the cation surplus concentration in the liquid phase and the $CO_2$ concentration in the gas phase, a chosen pH set point can be maintained, while the buffering capacity of the bicarbonate buffering system increases. The higher the cation surplus concentration the higher is the buffering capacity of the bicarbonate buffering system, and also the higher is the $CO_2$ concentration in the gas phase that is required to maintain a chosen pH level.

The buffering of the pH in the culture medium by elevation of both the cation surplus concentration in the culture medium and the $CO_2$ concentration in the gas phase can easily be applied to all kinds of bioreactors and photobioreactors, for example tubular, flat panel and bubble columns type photobioreactors. The pH at equilibrium can be set by setting the $CO_2$ concentration of the aeration gas by the use of two rotameters. One rotameter can control the flow rate of compressed air and one rotameter can control the flow rate of pure $CO_2$ at a certain percentage of the air flow rate.

In a preferred embodiment of the invention the method according to the present invention is used in a tubular bioreactor, especially photobioreactor and the gas phase is introduced into the liquid culture medium during step b) as slug flow, plug flow or bubble flow. In a preferred embodiment of the invention the method according to the present invention is used in a tubular photobioreactor and the gas phase is introduced into the liquid culture medium during step b) as slug flow.

The combination of the high $CO_2$ concentration in the gas phase and the cation surplus concentration according to the invention with a specific gas-liquid flow regime, preferably a slug flow, plug flow or a bubble flow, most preferably a slug flow, in at least one tube of a tubular bioreactor, especially photobioreactor results in surprising and synergistic advantages:

The transfer of both oxygen ($O_2$) and carbon dioxide ($CO_2$) from the liquid phase to the gas-phase and visa versa is improved, and at the same time the pH buffering capacity of the system is improved.

Furthermore due to the two-phase slug flow the surface to volume ratio of the culture medium is increased in comparison to tubes containing only fluid and the turbulence of the fluid is enhanced especially at the liquid-gas-interphase. The increase of the surface to volume ratio of the liquid phase means a smaller average light path, thereby allowing higher volumetric productivities.

Since carbon dioxide and oxygen compete at the active site of the important enzyme Ribulose-1,5-bisphosphate carboxylase oxygenase (RuBisCO) of the phototrophic organisms, carbon fixation by RuBisCO can be enhanced by increasing the ratio between dissolved inorganic carbon species and dissolved oxygen in the culture medium. Thus the inhibitory effect of high concentrations of dissolved oxygen in the medium on carbon fixation and hence growth is counteracted.

Due to these effects the fluid velocities of the moved culture medium in a tube can be limited to around 0.2 to 0.3 meter per second, thus limiting the energy consumption for the circulation pump or the air-lift system of the photobioreactor.

According to a preferred embodiment of the invention the fluid velocity of the moved culture medium is at most 0.5 meter per second, more preferably at most 0.3 meter per second, or even at most 0.2 meter per second. According to a preferred embodiment of the invention the fluid velocity of the moved culture medium is around 0.2 meter per second to 0.3 meter per second. Preferably the highest fluid velocity of the moved culture medium relates to the velocity in a tube of a tubular photobioreactor.

The ability to apply low fluid velocities in the tubes also leads to a decrease of the pressure drop over the entire circuit. The highest pressure in the system occurring at the beginning of a tube at the pressure side of a circulation pump and an air-pump/blower can be maintained below 0.2 bar. This allows the application of transparent tubes with smaller wall thickness and simple low pressure jointing techniques, thus reducing the investment costs.

According to a preferred embodiment of the invention the pressure in the at least one tube during step b) is at most 0.5 bar, more preferably at most 0.3 bar, most preferably at most 0.2 bar.

Additionally the two-phase slug flow prevents fouling at the inner wall of the transparent tubes. Accordingly the formation of a biofilm of microbiological cells attached to the inner wall of the tubes is prevented. Formation of such a biofilm is deleterious since such a biofilm will prevent the incident light from penetrating into the liquid culture medium and therefore inhibits growth of the phototrophic microorganisms.

In a preferred embodiment of the present invention the liquid culture medium contains no plastic particles which are used in the state of the art to prevent fouling.

In a preferred and alternative embodiment the methods and means according to the present invention are used to prevent fouling by the use of two-phase slug flow.

It has been surprisingly found that the method according to the present invention is not only advantageously if it is used for autotrophic growth of microorganisms under light but that it is also advantageously if it is used for heterotrophic growth of phototrophic microorganisms growing in the dark, e.g. at night, or for microorganisms growing per se heterotrophic.

In the dark photosynthesis will not occur. Due to respiration $O_2$ will be consumed by the microorganisms, while $CO_2$ is produced. The withdrawal of $O_2$ by the microorganisms from the liquid phase will cause a decrease of the level of dissolved $O_2$ in the liquid phase, while the production of $CO_2$ will cause a decrease of the pH. In the case of heterotrophic growth of microorganisms a carbon source is supplied to the liquid phase in the form of soluble organic molecules, e.g. sugars, organic acids, alcohols etc. Also in this case respiration occurs and $O_2$ will be consumed by the suspended microorganism, while $CO_2$ is produced.

It has been found that the method according to the present invention results in a better $CO_2/O_2$ ratio during a growth in the dark and during heterotrophic growth. Also in these cases the transfer of both oxygen ($O_2$) and carbon dioxide ($CO_2$) from the liquid phase to the gas-phase and visa versa is improved and at the same time the pH buffering capacity of the system is also improved. The microorganisms get enough $O_2$ from the liquid phase and are not inhibited by to high $CO_2$ amounts in the liquid phase.

Accordingly, the present invention refers also to the method used for autotrophic organisms in the dark and for heterotrophic organisms. If heterotrophic organisms are cultivated, the bioreactor used does not have to be a photobioreactor. Especially the tubes of a tubular bioreactor have then not to be translucent.

In a preferred embodiment, the present invention refers also to the method used for a culture of autotrophic and heterotrophic organisms in the dark. In a preferred embodiment, the present invention refers also to the method used for a culture of autotrophic and heterotrophic organisms in light.

By using the method according to the present invention it is possible to improve tubular bioreactors and especially photobioreactors in specific features.

In view of these effects the length of the at least one tube in a tubular photobioreactor can be increased up to ten fold, without the occurrence of accumulation of dissolved oxygen in the liquid phase to inhibitory levels, for example to more than 25 mg/l or the occurrence of an increase of the pH. The pH gradient over the entire circuit can be maintained in a designated pH range, for example between 8.0 and 8.4. The increased lengths of the at least one tube can be applied without increasing the average velocity of the fluid.

Accordingly the present invention also refers to a tubular bioreactor, comprising at least one tube, a circulation tank and a gas supply, wherein the at least one tube is connected as a loop to the circulation tank, wherein the gas supply is connected to the at least one tube, characterized in that the loop of the at least one tube has a length of at least 100 meter.

Accordingly the present invention also refers to a tubular photobioreactor, comprising at least one tube, a circulation tank and a gas supply, wherein the at least one tube is connected as a loop to the circulation tank, wherein at least a part of the at least one tube is translucent and wherein the gas supply is connected to the at least one tube, characterized in that the loop of the at least one tube has a length of at least 100 meter.

The tubular bioreactor and photobioreactor according to the present invention enables the construction of larger systems at relative lower costs, meaning lower investment costs per $m^3$ of system volume and per $m^2$ of ground surface required.

The ability to apply low fluid velocities in the tubes and the ability to decrease the pressure in the tubes allows the application of tubes, preferably transparent tubes with smaller wall thickness and simple low pressure jointing techniques, thus reducing the investment costs.

Accordingly the present invention also refers to a tubular bioreactor, comprising at least one tube, a circulation tank and a gas supply, wherein the at least one tube is connected as a loop to the circulation tank, wherein the gas supply is connected to the at least one tube, characterized in that the at least one tube is a plastic tube having a wall thickness of at most 1 mm.

Accordingly the present invention also refers to a tubular photobioreactor, comprising at least one tube, a circulation tank and a gas supply, wherein the at least one tube is connected as a loop to the circulation tank, wherein at least a part of the at least one tube is translucent and wherein the gas supply is connected to the at least one tube, characterized in that the at least one tube is a plastic tube having a wall thickness of at most 1 mm.

A preferred embodiment of the present invention refers to a tubular photobioreactor, comprising at least one tube, a circulation tank and a gas supply, wherein the at least one tube is connected as a loop to the circulation tank, wherein at least a part of the at least one tube is translucent and wherein the gas supply is connected to the at least one tube, characterized in that the loop of the at least one tube has a length of at least 100 meter, wherein the at least one tube is a plastic tube having a wall thickness of at most 1 mm.

The present invention also refers to tubular bioreactor, comprising at least one tube, a circulation tank and a gas supply, wherein the at least one tube is connected as a loop to the circulation tank, wherein the gas supply is connected to the at least one tube, characterized in that the at least one tube contains at least two pipes, wherein the pipes are connected by a push-fit fitting.

A preferred embodiment of the present invention refers to a tubular photobioreactor, comprising at least one tube, a circulation tank and a gas supply, wherein the at least one tube is connected as a loop to the circulation tank, wherein at least a part of the at least one tube is translucent and wherein the gas supply is connected to the at least one tube, characterized in that the loop of the at least one tube has a length of at least 100 meter, wherein the at least one tube is a plastic tube having a wall thickness of at most 1 mm and wherein the at least one tube contains at least two pipes, wherein the pipes are connected by a push-fit fitting.

By using the method according to the present invention allows a decrease of the pressure in the tubes and the use of longer tubes. These advantages allow surprisingly the use of tubes which are made of pipes of a given length. Due to the lower pressure in the tubes the pipes can be connected together without using glue or complicating mechanisms but with push-fit fittings which are easy to handle. The push-fit fittings can for example be made by thermo-forming of an accurately fitting muffle or sleeve on one and of a pipe wherein and end of another pipe having no thermoformed muffle or sleeve can be inserted. The pipes are preferably made of plastic, for example polyvinylchloride, especially PVC-U. The connection between the two pipes is airtight due to the friction force between the two pipes. Furthermore the connection between the pipes stays germfree. The advantages of the tubes made of pipes which are connected by a push-fit fitting are for example that the tubes can be build in a cheap way without using tools in a wished length, that the fitting is detachable, e.g. to clean the tube, that the fitting can be also translucent, that different components and/or materials can be connected, that the tube is stiffened by the fitting and that the clearance volume of the inner side of the pipes is minimized.

Preferably no glue used, however if wished a glue or a sealing mass can be used additionally to the push-fit fitting.

Preferably the bioreactor is a photobioreactor and wherein the at least one tube is translucent.

According to a preferred embodiment of the invention the tubular bioreactor or photobioreactor has several tubes, each being connected as a loop to the circulation tank. Accordingly the tubular photobioreactor has preferably several parallel loops of tubes.

Preferably the loop of the at least one tube has a length of at least 500 meter. Preferably the loop of the at least one tube has a length of around 1000 meter. Preferably the loop of the at least one tube has a length of at least 500 meter and at most 5000 meter, more preferably of at least 700 meter and at most 2000 meter.

Preferably the loops of all tubes of the tubular bioreactor or photobioreactor have a length of at least 100 meter, preferably of at least 500 meter, even more preferably of around 1000 meter. Preferably the loops of all tubes of the tubular bioreactor or photobioreactor have a length of at least 500 meter and at most 5000 meter, more preferably of at least 700 meter and at most 2000 meter.

Preferably the at least one tube is a plastic tube having a wall thickness of at most 600 μm, more preferably of at most 500 μm. The at least one tube cal also be a plastic tube having a wall thickness of around 150 μm. The at least one tube cal also be a plastic tube having a wall thickness of at least 100 μm, more preferably of at least 125 μm and at most 550 μm.

Preferably the at least one tube has an inner diameter of at least 25 mm, more preferably of at least 40 mm. Preferably the at least one tube has a inner diameter of around 6 cm. Preferably the at least one tube has a inner diameter of at most 150 mm, more preferably of at most 100 mm.

According to a preferred embodiment of the invention the at least one tube, more preferably all tubes of the tubular photobioreactor are translucent.

If the bioreactor is not used as a photobioreactor the tubes don't have to be translucent. In this case the tubes can be made for example from not translucent plastic material or metal.

According to a preferred embodiment of the invention the at least one tube, more preferably all tubes of the tubular photobioreactor are plastic tubes, for example polyethylene tubes, for example with a wall thickness of around 150 μm or polyvinyl chloride, for example with a wall thickness of at least 125 μm and at most 550 μm, preferably of around 500 μm. A preferred polyvinyl chloride used for the tubes is unplasticized polyvinyl chloride (PVC-U), According to a preferred embodiment of the invention the at least one tube, more preferably all tubes of the tubular photobioreactor are polyethylene tubes with al wall thickness of at least 100 μm to at most 200 μm, for example of around 150 μm.

According to an alternative embodiment of the invention the at least one tube, more preferably all tubes of the tubular photobioreactor are unplasticized polyvinyl chloride tubes with al wall thickness of at least 150 μm to at most 600 μm, for example of around 500 μm.

According to a preferred embodiment of the invention the at least one tube, more preferably all tubes of the tubular photobioreactor can have any profile, especially a circular, oval, triangular, rectangular, for example square, pentagonal, hexagonal, octagonal or other symmetric or asymmetric profile.

According to a preferred embodiment of the invention the tubular photobioreactor according to the invention is used in a method according to the present invention.

According to a preferred embodiment of the invention the tubular bioreactor according to the invention is used in a method for the cultivation of microorganisms in the bioreactor, wherein a gas phase containing at least 0.2 vol.-% $CO_2$ is introduced into a liquid culture medium containing the microorganisms, wherein the gas phase and the liquid culture medium form a slug flow in at least one tube, preferably in all tubes of the bioreactor, wherein the culture medium contains bicarbonate ions and/or carbonate ions in an amount of at least 3 mM, more preferably at least 10 mM (referred to the sum of bicarbonate ions and carbonate ions).

According to a preferred embodiment of the invention the tubular photobioreactor according to the invention is used in a method for the cultivation of phototrophic microorganisms, preferably algae or cyanobacteria, in the photobioreactor, wherein a gas phase containing at least 0.2 vol.-% $CO_2$ is introduced into a liquid culture medium containing the phototrophic organisms, wherein the gas phase and the liquid culture medium form a slug flow in at least one tube, preferably in all tubes of the photobioreactor, wherein the culture medium contains bicarbonate ions and/or carbonate ions in an amount of at least 3 mM, more preferably at least 10 mM (referred to the sum of bicarbonate ions and carbonate ions).

According to a preferred embodiment of the invention the tubular bioreactor according to the invention is used in a method for the cultivation of microorganisms in the bioreactor, wherein a gas phase containing at least 0.2 vol.-% $CO_2$ is introduced into a liquid culture medium containing the microorganisms, wherein the gas phase and the liquid culture medium form a slug flow in at least one tube, preferably in all tubes of the bioreactor, wherein the culture medium contains at least 1 mM, more preferably at least 10 mM of a substance selected from the group consisting of NaOH, $Na_2CO_3$, $NaHCO_3$, KOH, $K_2CO_3$, $KHCO_3$ and mixtures thereof.

According to a preferred embodiment of the invention the tubular photobioreactor according to the invention is used in a method for the cultivation of phototrophic microorganisms, preferably algae or cyanobacteria, in the photobioreactor, wherein a gas phase containing at least 0.2 vol.-% $CO_2$ is introduced into a liquid culture medium containing the phototrophic organisms, wherein the gas phase and the liquid culture medium form a slug flow in at least one tube, preferably in all tubes of the photobioreactor, wherein the culture medium contains at least 1 mM, more preferably at least 10 mM of a substance selected from the group consisting of NaOH, $Na_2CO_3$, $NaHCO_3$, KOH, $K_2CO_3$, $KHCO_3$ and mixtures thereof.

Preferably the culture medium contains at least 10 mM $NaHCO_3$, more preferably at least 20 mM $NaHCO_3$, for example around 40 mM $NaHCO_3$.

An advantage of the tubular photobioreactor according to the invention used for the disclosed methods is that an automated measurement and control of the $O_2$ concentration as applied in state-of-the art photo tubular reactors can be omitted.

In a preferred embodiment of the invention the tubular photobioreactor has no control elements for the oxygen concentration, especially the oxygen concentration in the culture medium.

The invention allows the replacement of automated measurement and control of pH, wherein extra $CO_2$ is injected into the gas supply when the pH value increases above a give set-point, by a manual setting of the $CO_2$-level of the gas supply by setting the flow rate of a gas phase, for example air, and pure $CO_2$ at the desired ration using two rotameters.

According to a preferred embodiment of the invention the tubular photobioreactor has two rotameters to set the flow rate of the gas phase and the $CO_2$ which is added to the gas phase.

According to a preferred embodiment of the invention the tubular photobioreactor has an air-pump, an air-blower or a fan to introduce a gas phase into the at least one tube.

According to a preferred embodiment of the invention the tubular photobioreactor has a device to circulate a liquid, especially a culture medium through the at least one tube. According to a preferred embodiment of the invention the tubular photobioreactor has a pump or an air-lift system to circulate a liquid, especially a culture medium through the at least one tube. Preferably the tubular photobioreactor has a pump to circulate a liquid through the at least one tube.

In photobioreactors using an a conventional gas exhaust in the separation tank the exhausting gas from the top of separation tank into the atmosphere will lead to large losses of applied $CO_2$. This is not desirable and can be prevented by circulating the gas phase by means of an air pump. To keep the carbon level in the system sufficiently high the circulated aeration flow is fed with $CO_2$ enriched air or with pure $CO_2$ at a point of the gas circuit just before the gas is injected in to the culture medium. Degassing can take place through a safety valve at a point in the gas circuit at the top of the photobioreactor. The flow rate of the $CO_2$ supply can be much smaller than that of the circulated gas phase and will typically be in the range of 1-5%.

According to a preferred embodiment of the invention the tubular photobioreactor is a closed system, wherein the gas supply is not only connected to the at least one tube but also to the top of the circulation tank and has a $CO_2$ supply.

According to a preferred embodiment of the invention the tubular photobioreactor is a closed system, wherein the gas supply is not only connected to the at least one tube but also to the top of the circulation tank and has a $CO_2$ supply and wherein the circulation tank has a gas exhaust.

In a preferred embodiment of the invention the gas phase is introduced into the liquid culture as slug flow at the beginning of the at least one tube and is recirculated through the at least one tube into the circulation tank. Preferably a part of the gas phase in the circulation tank is introduced into the gas supply, where it can be preferably enriched with $CO_2$ and again introduced into the liquid culture as slug flow at the beginning of the at least one tube.

According to a preferred embodiment of the invention the gas supply is designed to be able to introduce a gas phase into a liquid phase in the at least one tube creating a slug flow. The forming of a slug flow is mainly dependent on the diameter of the tubes and the velocity and the resulting amount of the gas phase and the liquid phase. A person skilled in the art knows how to form a slug flow by choosing appropriate velocities for a given diameter. A person skilled in the art also knows how to adapt and connect the gas supply to the at least one tube so that a slug flow can be formed in the tube.

The present invention also refers to the use of a photobioreactor, preferably a tubular photobioreactor in a method according to the invention or in a method described herein. Preferably the tubular photobioreactor is a tubular photobioreactor according to the present invention.

The increase of the turbulence, especially at the liquid-gas-interface allows thorough mixing of the culture medium containing the phototrophic microorganisms along the light gradient and thereby light/dark cycles can be lower then one per second, i.e. lower than 1 Hz. This level of turbulence/mixing/light-dark-cycles can be achieved at lower fluid velocities and in tubes with larger inner diameters and therefore at much lower auxiliary energy supply then in state-of-the-art single-phase tubular reactors. State-of-the-art tubular photobioreactors require auxiliary energy supply of more then 2000 Watt per $m^3$ culture medium, while application of the a slug flow in combination with an increased carbonate buffering system, allowing longer loops, while maintaining low fluid velocities leads to a reduction of the auxiliary energy input to approximately 200 Watt per $m^3$ culture medium.

Preferred is a use of a tubular photobioreactor, preferably a tubular photobioreactor according to the present invention in a method according to the invention or in a method described herein, wherein the photobioreactor has an auxiliary energy input of at most 500 $W/m^3$, more preferably of at most 300 $W/m^3$ related to the volume of the liquid culture medium in the photobioreactor.

The present invention also refers to the use of a tube or a pipe having a wall thickness of at most 1 mm in a tubular bioreactor according to the present invention. The present invention also refers to the use of a tube or a pipe having a wall thickness of at most 1 mm in a method according to the invention. Preferably the tube or pipe is a tube or pipe with the preferred features for tubes and pipes described herein, for example an translucent unplasticized polyvinylchloride tubes with al wall thickness of at least 150 μm to at most 600 μm, for example of around 500 μm.

The present invention also refers to a tubular bioreactor, comprising at least one tube, a circulation tank and a gas supply, wherein the at least one tube is connected as a loop to the circulation tank, wherein the gas supply is connected to the at least one tube, characterized in that the at least one tube is a plastic tube having a wall thickness of at most 1 mm and that the at least one tube builds at least one reaction section which is substantially horizontal or has a inclination of at least 0.1 degree to at most 3.0 degree.

The present invention also refers to a tubular bioreactor, comprising at least one tube, a circulation tank and a gas supply, wherein the at least one tube is connected as a loop to the circulation tank, wherein the gas supply is connected to the at least one tube, characterized in that the loop of the at least one tube has a length of at least 100 meter and that the at least one tube builds at least one reaction section which is substantially horizontal or has a inclination of at least 0.1 degree to at most 3.0 degree.

The present invention also refers to a tubular bioreactor, comprising at least one tube, a circulation tank and a gas supply, wherein the at least one tube is connected as a loop to the circulation tank, wherein the gas supply is connected to the at least one tube, characterized in that the at least one tube contains at least two pipes, wherein the pipes are connected by a push-fit fitting and that the at least one tube builds at least one reaction section which is substantially horizontal or has a inclination of at least 0.1 degree to at most 3.0 degree.

In a preferred embodiment the at least one reaction section is substantially horizontal.

In a preferred embodiment the at least one reaction section has a slight inclination. In a preferred embodiment the at least one reaction section has a inclination of at least 0.1 degree to at most 3.0 degree. In a preferred embodiment the at least one reaction section has a inclination of at least 0.1 degree to at most 2.5 degree. In a preferred embodiment the at least one reaction section has a inclination of at least 0.1 degree, more preferably of at least 0.2 degree even more preferably of at least 0.5 degree. In a preferred embodiment the at least one reaction section has a inclination of at most 3.0 degree, more preferably of at most 2.5 degree even more preferably of at most 2.0 degree, even more preferably of at 1.5 degree. Degrees refer to the angle measured in relation to the horizontal.

In a preferred embodiment the most or all of the at least one tube builds the at least one reaction section.

The inventors surprisingly found that a slight inclination of the reaction section leads to a more regular slug flow. This leads to an improved transfer of $CO_2$ and $O_2$ between gas and liquid and contrawise. Furthermore due to the improved transfer of $CO_2$ and $O_2$ it is possible to use only gas injection to move the liquid. So a liquid pump can be omitted, and this will allow the cultivation of fragile organisms, e.g. fragile algae.

Accordingly the tubular photobioreactors having at least one tube building at least one tube builds at least one reaction section which has a inclination of at least 0.1 degree to at most 3.0 degree, have no pump and more preferably also no air-lift system to circulate a liquid through the at least one tube.

The inclination should be not too high since this leads to increased energy needed for the moving of the liquid.

As preferred embodiments, the tubular photobioreactors having at least one tube building at least one reaction section which is substantially horizontal or has a inclination of at least 0.1 degree to at most 2.5 degree, can have some or all of the preferred features described in this description for bioreactors and especially photobioreactors.

The present invention also refers to the use of these photobioreactors in a method described in the present description, preferably in a method for the cultivation of organisms in a bioreactor, including the steps: a) providing a liquid culture medium containing the organisms in the bioreactor and b) cultivating the organisms in the bioreactor, wherein the liquid culture medium contains a bicarbonate buffer system containing bicarbonate ions and/or carbonate ions in an amount of at least 3 mM (referred to the sum of bicarbonate ions and carbonate ions) and wherein during at least a time segment of step b) the liquid culture medium is moved, characterized in that during at least a time segment of step b) a gas phase containing at least 0.2 vol.-% $CO_2$ is introduced into the culture medium.

Alternative and preferred embodiments of the invention are:

1. alternative embodiment: A method for the cultivation of organisms in a bioreactor, including the steps:
a) providing a liquid culture medium containing the organisms in the bioreactor and
b) cultivating the organisms in the bioreactor,
wherein the liquid culture medium contains a bicarbonate buffer system containing bicarbonate ions and/or carbonate ions in an amount of at least 3 mM (referred to the sum of bicarbonate ions and carbonate ions) and wherein during at least a time segment of step b) the liquid culture medium is moved, characterized in that during at least a time segment of step b) a gas phase containing at least 0.2 vol.-% $CO_2$ is introduced into the culture medium.
2. preferred embodiment: The method according to embodiment 1, wherein the bioreactor is a photobioreactor and wherein the organisms are phototrophic organisms, preferably are algae.
3. preferred embodiment: The method according to embodiments 1 or 2, wherein the bioreactor is a tubular bioreactor, preferably a tubular photobioreactor.
4. preferred embodiment: The method according to embodiment 3, wherein the gas phase is introduced into the liquid culture medium during step b) as slug flow.
5. preferred embodiment: The method according to any one of the preceding embodiments, wherein the bioreactor is a tubular bioreactor according to embodiments 6 to 13.
6. alternative embodiment: A tubular bioreactor (1), comprising at least one tube (2), a circulation tank (3) and a gas supply (5,6), wherein the at least one tube (2) is connected as a loop to the circulation tank (3), wherein the gas supply (5) is connected to the at least one tube (2), characterized in that the at least one tube (2) is a plastic tube having a wall thickness of at most 1 mm.
7. alternative embodiment: A tubular bioreactor (1), preferably a bioreactor according to embodiment 6, comprising at least one tube (2), a circulation tank (3) and a gas supply (5,6), wherein the at least one tube (2) is connected as a loop to the circulation tank (3), wherein the gas supply (5) is connected to the at least one tube (2), characterized in that the loop of the at least one tube (2) has a length of at least 100 meter.
8. alternative embodiment: A tubular bioreactor (1), preferably a bioreactor according to embodiments 6 or embodiment 7, comprising at least one tube (2), a circulation tank (3) and a gas supply (5,6), wherein the at least one tube (2) is connected as a loop to the circulation tank (3), wherein the gas supply (5) is connected to the at least one tube (2), characterized in that the at least one tube (2) contains at least two pipes, wherein the pipes are connected by a push-fit fitting.
9. preferred embodiment: A tubular bioreactor according to any of embodiments 6 to 8, wherein the bioreactor (1) is a photobioreactor and wherein the at least one tube (2) is translucent.
10. preferred embodiment: The tubular bioreactor according to any of embodiments 6 to 9, having an air-pump (7), an air-blower or a fan to introduce a gas phase (10) into the at least one tube (2) and having a pump (4) or an air-lift system to circulate a liquid (8) through the at least one tube (2).
11. preferred embodiment: The tubular bioreactor according to any of embodiments 6 to 10, wherein the bioreactor (1) is a closed system and wherein the gas supply (5) is connected to the top of the circulation tank (3) and to a $CO_2$ supply (6).
12. preferred embodiment: The tubular bioreactor according any of embodiments 6 to 11, wherein the bioreactor has no control elements for the oxygen concentration.
13. preferred embodiment: The tubular bioreactor according any of embodiments 6 to 12, wherein the gas supply (5) is designed to be able to introduce a gas phase (10) into a liquid phase (8) in the at least one tube (2) creating a slug flow (9).
14. alternative embodiment: Use of a bioreactor, preferably a tubular bioreactor according to any of embodiments 6 to 13, in a method according to any of embodiments 1 to 4.
15. preferred embodiment: Use according to embodiment 14, wherein the bioreactor is a photobioreactor.

16. alternative embodiment: Use of a tube or a pipe having a wall thickness of at most 1 mm in a tubular bioreactor according to any of embodiments 6 to 13 or in a method according to any of embodiments 1 to 5.

BRIEF DESCRIPTION OF THE DRAWINGS

The invention will be described in more detail, without limiting the scope of the invention, in the figures and following examples.

Figure 1:
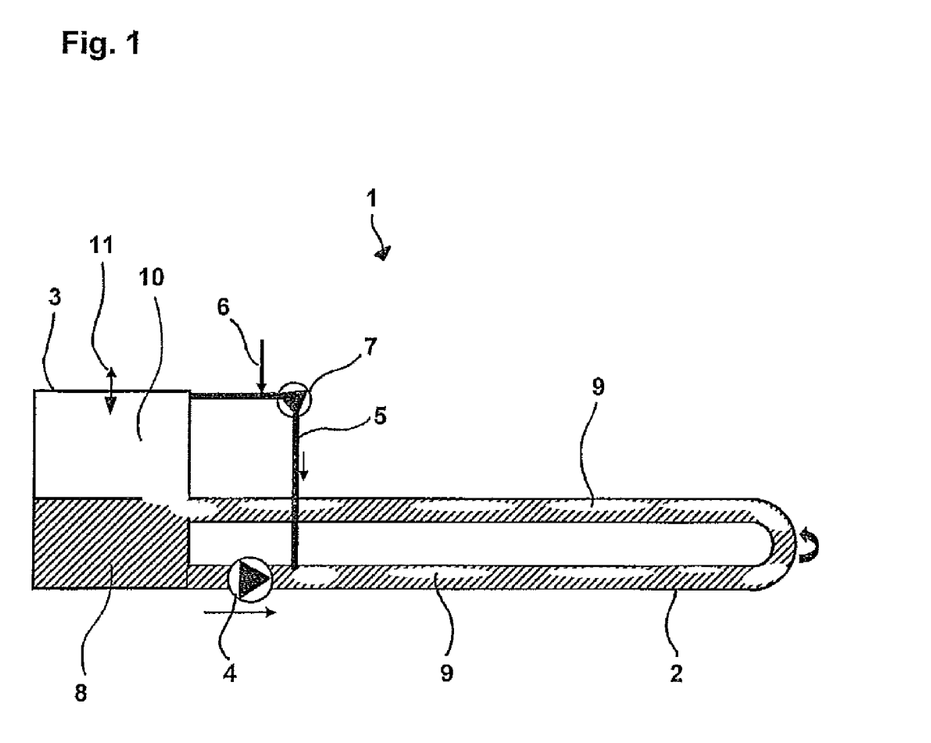
FIG. 1 shows schematically a tubular photobioreactor according to the present invention.

FIG. 1 shows schematically a tubular photobioreactor 1 according to the present invention which is used in a method described herein. The photobioreactor 1 comprises a tube 2 and a circulation tank 3.

DETAILED DESCRIPTION

The tube can be made of a plastic material, having a thin wall thickness of for example at least 100 µm and at most 600 µm and a inner diameter of around 6 cm. The tube can be longer than tubes of known photobioreactors, e.g. at least 180 meter. Of course the photobioreactor 1 can have several tubes 2. The tube 2 is arranged as a loop, wherein a liquid culture medium 8 can circulate from the bottom of the circulation tank 3 through the tube 2 back to the circulation tank 3.

The circulation tank 3, also known as collection tank or degassing tank contains culture medium 8 with microorganisms and a gas phase 10, preferably compressed atmospheric air. The circulation tank 3 has a gas liquid surface that is sufficiently large to allow gas-liquid separation at given gas- and liquid flow speeds.

Each loop can have at least one turn, but can also have 3, 5 or a higher number of turns to from a serpentine like structure before the tube ends in the gas-liquid separation tank. The tubes can be mounted horizontally or at a (slight) slope. The turns can be mounted in the horizontal plane or in a tilted plane. When turns are mounted in a tilted plan the tube after the turn, or after each turn in the case each loops contains more then one turn, can be mounted in a plane elevated to the plane in which the tube before the turn is mounted.

Of course the bioreactor can have additional features known to a person skilled in the art, for example a liquid exhaust and a liquid supply in the circulation tank 3.

The culture medium is circulated from the circulation tank 3 through the tube 2 via a liquid pump 4.

The gas phase 10 can leave the circulation tank 3 via a gas exhaust 11. However, at least some of the gas phase 10 is pumped via an air pump 7 through a gas supply 5 into the culture medium 4. The gas phase 10 can be enriched with $CO_2$, e.g. to a $CO_2$ concentration of at least 0.2 vol.-% via a supply 6 for pure $CO_2$ or for $CO_2$ enriched air. Since the gas phase 10 in the circulation tank 3 contains already CO2 which was not used by the microorganisms and evaporates from the culture medium 8 in the circulation tank 3, the $CO_2$ amounts which have to be provided by the supply 6 can be reduced to obtain a gas phase containing at least 0.2 vol.-% $CO_2$.

The gas phase 10 is introduced into the first section of the tube 2, in view of the circulation-direction of the culture medium 8 in an amount and a velocity to obtain a slug flow consisting of the culture medium 8 and gas bubbles 9, containing increased $CO_2$ amounts. The culture medium contains a cation surplus concentration, e.g. by the addition of at least 1 mM or preferably at least 10 mM $NaHCO_3$. This results together with the $CO_2$ concentration in the gas bubbles and the forming of a slug flow to the advantages disclosed herein, which allow the use of longer tubes 2 than the tubes of the state of the art and of tubes 2 with a thinner wall thickness than the one of tubes used in the state of the art.

The gas bubbles 9 leave the culture medium 8 at the end of the tube 2 and diffuse into the gas phase 10 of the circulation tank 3.

Figure 2:
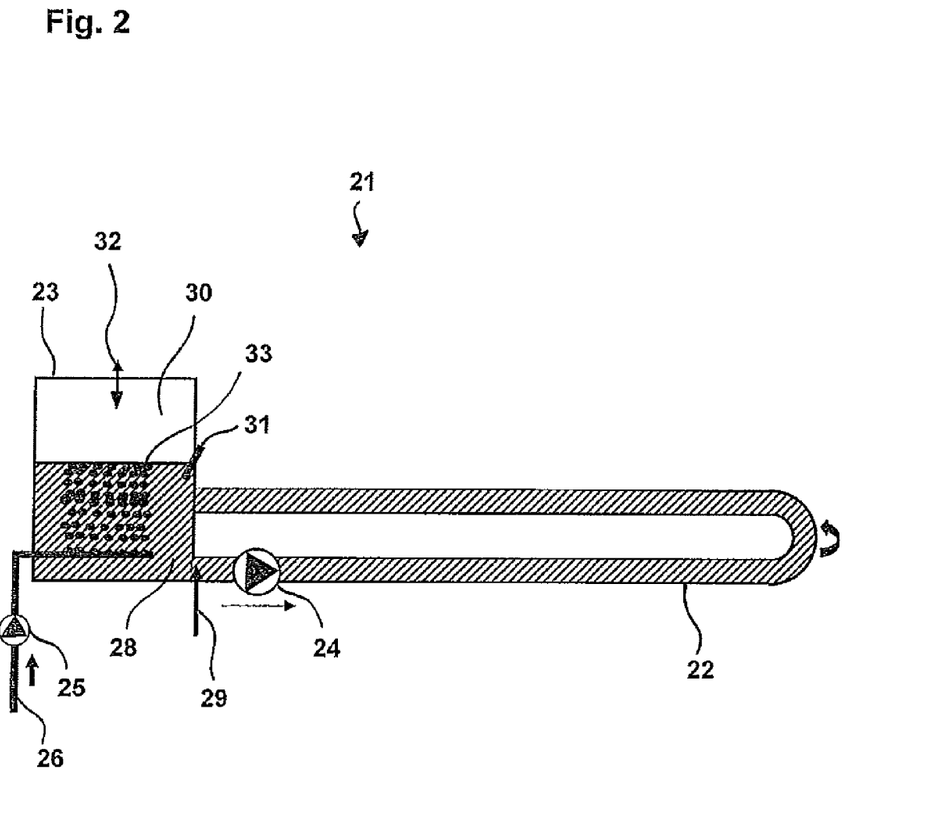
FIG. 2 shows schematically a tubular photobioreactor according to the state of the art used in the comparative example 3.

FIG. 2 shows schematically a tubular photobioreactor 21 according to the state of the art as it was used in the comparative example 3.

The photobioreactor 21 comprises again a tube 22 and a circulation tank 23. Culture medium 28 is circulated through the tube 22 via a liquid pump 24.

However the gas phase 30 is not circulated through the tube 22 of the reactor. Aeration to establish mass transfer between the liquid and the gas phase takes place in the circulation tank 23 via a supply 26, an air pump 25 and a sparger 27 providing air as bubbles 33. Furthermore the gas phase 30 can leave the circulation tank 23 via a gas exhaust 32. $CO_2$ is injected directly in the culture medium 28 via a supply 29 at the beginning of the tube 22 of the reactor 21 when the pH measured by a pH-meter 31 exceeds a given set point. No slug flow is formed but the tube 22 is completely filled with culture medium 28. Such a conventional mode of operation dissolved $O_2$ is removed from the culture medium 28 by aeration of the circulation tank 23. This leads to levels of dissolved $O_2$ in the culture medium 28 in the tube 22 of for example more than 50 mg/L. These high levels of dissolved $O_2$ inhibit the photosynthesis process and hence the growth of phototrophic organisms.

Example 1

40 mM of $NaHCO_3$ were added to the culture medium of 3 liter bubble columns positioned vertically in temperature controlled incubators. The diameter of these cylindrical columns is 6 cm; the height of the liquid level in each column is about 0.7 m. The volume of the liquid is 2 liters. The medium is aerated from the bottom of the each column with air enriched with 2% $CO_2$. The aeration rate is 0.5 liter/min. After equilibration of the gas and the liquid phase pH 8.4 is achieved in the liquid phase. The bubble columns are inoculated with cells of the micro algae *Nannochloropsis*. Bubble columns are continuously illuminated from two sides using fluorescent tubes with light intensity from each side of around 100 umol/m²/s. In about 2 weeks the culture grows autotrophically, and algal biomass increases from 0.1 to 3 g/l. During cultivation pH only slowly increases to about pH 8.6 when the culture is illuminated. In the dark pH does not drop below pH 8.4. Thus in this setup no actively regulated pH control (by measuring the pH with a probe and sparging the system with $CO_2$ when the pH increases above a given set point) is required. This method can also be applied to large scale production plants with arrays of bubble columns or flat panel reactors.

Example 2

A conventional tubular PBR as it is shown in FIG. 2 was used to cultivate *Nannochloropsis*. This was compared to cultivation of *Nannochloropsis* in an alternative operational mode using an elevated bicarbonate/carbonate buffer in the liquid phase and elevated $CO_2$ concentrations in the gas phase and application of a slug flow in the tubular part of the PBR as shown in FIG. 1. Compared to the conventional operation the bicarbonate/carbonate buffer was increased by the addition of 40 mM of $NaHCO_3$ in the liquid phase. The gas phase applied in the conventional operation was atmospheric air and contained in the alternative mode 2% $CO_2$. In the conventional operation no slug flow was formed in the tubular part of the PBR.

Illumination levels by natural sunlight were similar for both cases.

While in the in the conventional operation mode dissolved $O_2$ levels increase during the day to maximum levels of 45 mg/L, the dissolved oxygen $O_2$ level did not exceed 22 mg/L when the alternative mode was applied.

Furthermore, in the conventional operation mode, the aeration of the liquid phase in the circulation tank to remove dissolved $O_2$, is accompanied by unwanted removal of $CO_2$. The total daily amount of $CO_2$ loss from the PBR was between 10 to 30 kg when operated in the conventional mode and only 1 to 3 kg when operated in the alternative mode.

Example 3

In tubular photobioreactors the method of pH control according to the present invention can be applied when the gas phase is also circulated through the tubular part of the reactor. The schematic set up for a tubular photobioreactor used in this example is shown in FIG. 1.

40 mM of $NaHCO_3$ were added to the culture medium of a 600 liter tubular photo bioreactor. The tubular loops of this system consist of one tube with a 6 cm diameter and a length of approximately 180 m. The volume of the tubular loop is accordingly around 500 liters. The volume of the circulation tank is 100 liters. The volume of the liquid phase is approximately 400 liter and that of the gas phase 200 liter.

The flow rate of the air pump is 4 $m^3$ per hour. The flow rate of the liquid pump is 2.5 $m^3$ per hour.

The $CO_2$ concentration of the gas supply is controlled by two rotameters and set at 2%. The flow rate of the gas supply is 0.2 $m^3$ per hour. In combination with a cation surplus of 40 mM this results in a pH-value at equilibrium of pH 8.4.

Also in this configuration the pH of the liquid medium throughout the reactor is very well maintained by increasing both the cation surplus concentration of the liquid phase and the $CO_2$ concentration in the gas phase and thereby increasing the buffering capacity of the bicarbonate system.

The behaviour of the gas and liquid phase in the tubular loop in this case can be described as a typical "slug flow". This two-phase "slug flow" enables thorough mixing of the liquid phase along the light gradient (which is vertical, perpendicular on the tubular axis) and thereby light/dark cycles of less than 1 Hz, while the auxiliary energy supply is only 200 W per $m^3$ of cultures. In comparison with auxiliary energy supply of state-of-the-art tubular PBRs of more than 2000 W per $m^3$ this is a huge improvement on the economy of the process in terms of energy costs. Due to the slug flow, the light path is on average much smaller than the tube diameter of 6 cm, thereby allowing higher volumetric productivities.

Further more the "slug flow" also enables the prevention of fouling and the formation of a bio-film on the inside of the tube by the absence of a laminar layer close to the surface of the tube that exists in normally operated tubular reactors.

Stabilization of the pH of the liquid medium by increasing both the cation surplus concentration of the liquid phase and the $CO_2$ concentration of the gas phase, also leads to the stabilization of the dissolved oxygen concentration in the liquid medium.

The invention claimed is:

1. A method for the cultivation of organisms in a tubular photobioreactor, including the steps:
    (a) providing a liquid culture medium containing the organisms in the photobioreactor; and
    (b) cultivating the organisms in the photobioreactor over time;
    wherein the photobioreactor is a closed system, and comprises at least one tube, a circulation tank, a gas supply and at least one reaction section with an inclination of at least 0.1 degrees with respect to horizontal;
    wherein the at least one tube is connected as a loop of at least 100 meters to the circulation tank, the gas supply is connected to the at least one tube, the gas supply is also connected to the top of the circulation tank and the gas supply is also connected to a $CO_2$ supply; and
    wherein the liquid culture medium contains a bicarbonate buffer system containing bicarbonate ions and/or carbonate ions in an amount of at least 3 mM (referred to the sum of bicarbonate ions and carbonate ions) and wherein during at least a time segment of step (b), the liquid culture medium is moved, and a gas phase containing at least 0.2 vol.-% $CO_2$ is introduced into the culture medium as slug flow or plug flow, and wherein a mixture of the gas phase and the culture medium passes through the photobioreactor as two phase flow with the gas phase moving faster through the at least one tube than the liquid culture medium.

2. The method according to claim 1, wherein the organisms are phototrophic organisms.

3. The method according to claim 1, wherein the organisms are algae.

4. The method according to claim 1, wherein the photobioreactor is a tubular photobioreactor.

5. The method according to claim 1, wherein the at least one tube is a plastic tube having a wall thickness of at most 1 mm.

6. The method according to claim 5, wherein the at least one tube contains at least two pipes, wherein the pipes are connected by a push-fit fitting.

7. The method according to one of claim 5 or 6, including an air-pump, an air-blower or a fan to introduce a gas phase into the at least one tube and having a pump or an air-lift system to circulate a liquid through the at least one tube.

8. The method according to one of claim 5 or 6, wherein the photobioreactor has no control elements for the oxygen concentration.

9. The method according to one of claim 5 or 6, wherein the gas supply is designed to be able to introduce a gas phase into a liquid phase in the at least one tube creating a slug flow.

10. The method according to one of claim 5 or 6, wherein the at least one tube is translucent.

11. The method according to claim 1, wherein the at least one tube is a plastic tube having a wall thickness of at most 1 mm and wherein the at least one tube builds at least one reaction section which or has an inclination of at least 0.1 degree to at most 3.0 degrees.

12. A method for the cultivation of organisms in a bioreactor, including the steps:
    (a) providing a tubular photobioreactor;
    (b) providing a liquid culture medium containing the organisms in the bioreactor; and
    (c) cultivating the organisms in the bioreactor over time;
    wherein the photobioreactor is a closed system, and comprises at least one tube, a circulation tank, a gas supply and at least one reaction section with an inclination of at least 0.1 degrees with respect to horizontal;

wherein the at least one tube is connected as a loop of at least 100 meters to the circulation tank, the gas supply is connected to the at least one tube, the gas supply is also connected to the top of the circulation tank and the gas supply is also connected to a $CO_2$ supply; and wherein the liquid culture medium contains a bicarbonate buffer system containing bicarbonate ions and/or carbonate ions in an amount of at least 3 mM (referred to the sum of bicarbonate ions and carbonate ions) and wherein during at least a time segment of step (b), the liquid culture medium is moved, and a gas phase containing at least 0.2 vol.-% $CO_2$ is introduced into the culture medium, and wherein a mixture of the gas phase and the culture medium passes through the tubular photobioreactor as two phase flow with the gas phase moving faster through the at least one tube than the liquid culture medium.

13. The method according to claim 12, wherein the at least one tube is a plastic tube having a wall thickness of at most 1 mm.

14. The method according to claim 12, wherein the organisms are algae.

15. The method according to claim 12, wherein the at least one tube builds at least one reaction section which has an inclination of at least 0.1 degree to at most 3.0 degrees.

16. The method according to claim 12, wherein the at least one tube contains at least two pipes, wherein the pipes are connected by a push-fit fitting.

* * * * *